US006809068B1

(12) United States Patent
Küpper et al.

(10) Patent No.: US 6,809,068 B1
(45) Date of Patent: *Oct. 26, 2004

(54) USE OF LUBRICANTS BASED ON POLYSILOXANES

(75) Inventors: Stefan Küpper, Langenfeld (DE); Michael Schneider, Jüchen (DE); Walter Grosse Böwing, Dormagen (DE); Alfred Laufenberg, Dormagen (DE); Harald Kluschanzoff, Mettmann (DE)

(73) Assignee: Ecolab Inc., St. Paul, MN (US)

( * ) Notice: Subject to any disclaimer, the term of this patent is extended or adjusted under 35 U.S.C. 154(b) by 810 days.

This patent is subject to a terminal disclaimer.

(21) Appl. No.: 09/655,543

(22) Filed: Sep. 6, 2000

(30) Foreign Application Priority Data

Sep. 7, 1999 (DE) .......................................... 199 42 536

(51) Int. Cl.⁷ ........................ C10M 173/02; B65G 45/02
(52) U.S. Cl. ........................ 508/208; 508/209; 508/215; 198/500
(58) Field of Search ................................ 508/215, 208

(56) References Cited

U.S. PATENT DOCUMENTS

| | | | |
|---|---|---|---|
| 3,011,975 A | 12/1961 | Nitzsche et al. | |
| 3,213,024 A | 10/1965 | Blake et al. | |
| 3,664,956 A | 5/1972 | Messina et al. | |
| 3,860,521 A | 1/1975 | Aepli et al. | ................ 252/34.7 |
| 3,981,812 A | 9/1976 | Zletz | |
| 4,149,624 A | 4/1979 | Douty et al. | |
| 4,162,347 A | 7/1979 | Montgomery | |
| 4,163,079 A * | 7/1979 | Beafore | ................ 428/411 |
| 4,248,724 A | 2/1981 | MacIntosh | |
| 4,289,671 A | 9/1981 | Hernandez | |
| 4,290,810 A * | 9/1981 | Montgomery | ................ 106/13 |
| 4,324,671 A | 4/1982 | Christian et al. | |
| 4,436,200 A | 3/1984 | Hodlewski et al. | |
| 4,652,386 A | 3/1987 | Alberts et al. | |
| 4,719,022 A | 1/1988 | Hyde | |
| 4,828,727 A | 5/1989 | McAninch | |
| 4,839,067 A | 6/1989 | Jansen | ................ 252/11 |
| 4,929,375 A | 5/1990 | Rossio et al. | |
| 5,009,801 A | 4/1991 | Wider et al. | |
| 5,073,280 A | 12/1991 | Rossio et al. | |
| 5,160,646 A | 11/1992 | Scheld | |
| 5,174,914 A | 12/1992 | Gutzmann | |
| 5,182,035 A | 1/1993 | Schmidt et al. | |
| 5,191,779 A | 3/1993 | Imaja et al. | |
| 5,334,322 A | 8/1994 | Williams, Jr. | |
| 5,352,376 A | 10/1994 | Gutzmann | |
| 5,352,378 A * | 10/1994 | Mathisen et al. | ................ 252/54 |
| 5,486,316 A | 1/1996 | Bershas et al. | |
| 5,534,172 A * | 7/1996 | Perry et al. | ................ 508/156 |
| 5,549,836 A | 8/1996 | Moses | |
| 5,559,087 A | 9/1996 | Halsrud et al. | |
| 5,663,131 A | 9/1997 | Winicov et al. | |
| 5,672,401 A | 9/1997 | Anglin et al. | |
| 5,681,628 A | 10/1997 | Niederst et al. | |
| 5,863,874 A | 1/1999 | Person Hei et al. | |
| 5,869,436 A | 2/1999 | Lindman | |
| 5,925,601 A | 7/1999 | McSherry | |
| 5,935,914 A | 8/1999 | Theyssen et al. | |
| 6,207,622 B1 * | 3/2001 | Li et al. | ................ 508/208 |
| 6,288,012 B1 * | 9/2001 | Li et al. | ................ 508/113 |
| 6,427,826 B1 * | 8/2002 | Li et al. | ................ 198/500 |
| 6,495,494 B1 * | 12/2002 | Li et al. | ................ 508/206 |
| 6,509,302 B2 * | 1/2003 | Li et al. | ................ 508/208 |
| 6,576,298 B2 * | 6/2003 | Bennett et al. | ................ 427/424 |

FOREIGN PATENT DOCUMENTS

| | | |
|---|---|---|
| CA | 1157456 A | 11/1983 |
| DE | 2 313 330 | 10/1973 |
| DE | 36 31 953 | 3/1988 |
| DE | 39 05 548 | 9/1990 |
| DE | 42 06 506 | 9/1993 |
| DE | 44 23 203 A1 | 1/1995 |
| EP | 0 359 330 | 3/1990 |
| EP | 0 372 628 | 5/1993 |
| EP | 0 629 234 | 11/1995 |
| EP | 0 844 299 | 5/1998 |
| GB | 1564128 | 4/1980 |
| JP | 57003892 | 1/1982 |
| JP | 6-136377 | 5/1994 |
| JP | 10053679 A | 8/1996 |
| JP | 10059523 | 3/1998 |
| NL | 9300742 | 5/1993 |
| WO | WO 94/03562 | 2/1994 |
| WO | 96/08601 | 3/1996 |
| WO | WO 01/07544 A1 | 2/2001 |

OTHER PUBLICATIONS

*Guidelines for an Industrial Code of Pratice for Refillable PET Bottles, Edition 1.* UNESDA–CESDA, 1993–1994.
Co–pending patent application Ser. No. 09/655,544 entitled: "Fluorine–Containing Lubricants", filed Sep. 6, 2000.
Co–pending patent application Ser. No. 09/731,118 entitled: "Improvements in the Transport of Containers on Conveyors", filed Dec. 6, 2000.
Patent Abstracts of Japan, JP 09–095692 A. "Water–Soluble Lubricant Composition." Apr. 8, 1997.
Patent Abstracts of Japan, JP 06–17278 A. "Lubricant for Conveyor." Jun. 21, 1994.
Patent Abstracts of Japan, JP 06–136377 A. "Bacterial Lubricant." May 17, 1994.
Huber et al. "Silicone Oils: Synthesis, Production, Characteristics, and Applications". Presented at the 4$^{th}$ Annual Internal Colloquium "Synthetic Lubricants and Operating Fluids", Technical Academy of Esslingen, Jan. 10–12, 1084, Ostifildem, and English translation.

(List continued on next page.)

*Primary Examiner*—Ellen M. McAvoy
(74) *Attorney, Agent, or Firm*—Merchant & Gould P.C.

(57) ABSTRACT

The invention relates to the use of at least one polysiloxane in lubricant formulations for reducing friction between conveyor belts and the articles transported thereon. The invention also relates to lubricants containing other additives besides polysiloxane.

60 Claims, No Drawings

OTHER PUBLICATIONS

"A fracture mechanics approach to environmental stress cracking in poly(ethyleneterephthalate)," *Polymer*, vol. 39 No. 3, pp. 75–80 (1998).

"Environmental Stress Cracking Resistance of Blow Molded Poly(Ethylene Terephthalate) Containers," *Polymer Engineering and Science*, vol. 32, No. 6, pp. 393–399 (Mar. 1992).

"Environmental Stress Cracking in PET Carbonated Soft Drink Containers," Eric J. Moskala, Ph.D., Eastman Chemical Company, presented at Bev Tech 98 (Savannah, GA).

Lubrication and Lubricants, *Encyclopedia of Chemical Technology*, vol. 15, pp. 463–517.

Material Safety Data Sheet for Lubostar CP (May 3, 2000).

"The Alternative to Soap and Water for Lubricating Conveyor Lines," *Food & Drink Business*, pp. 35–36 (Jan. 1998).

* cited by examiner

USE OF LUBRICANTS BASED ON POLYSILOXANES

This invention relates to the use of polysiloxane-containing lubricant formulations. The invention also relates to lubricants containing polysiloxanes and other additives.

In the food industry and especially in beverage factories, the containers to be filled in the bottling plants are conveyed by conveyors differing in design and constituent materials, for example by platform conveyors or chain-like arrangements which are generally referred to hereinafter as chain conveyors. The conveyors establish the connection between the various optional treatment stages of the bottling process such as, for example, the unpacker, bottle washer, filler, closer, labeller, packer, etc. The containers may assume various forms, more particularly glass and plastic bottles, cans, glasses, casks, beverage containers (kegs), paper and paperboard containers. To guarantee uninterrupted operation, the conveyor chains have to be suitably lubricated to avoid excessive friction with the containers. Dilute aqueous solutions containing suitable friction-reducing ingredients are normally used for lubrication. The chain conveyors are contacted with the aqueous solutions by dipping or spraying, for example, the corresponding lubrication systems being known as dip lubrication or automatic belt lubrication or central chain lubrication systems.

The chain lubricants hitherto used as lubricants are mostly based on fatty acids in the form of their water-soluble alkali metal or alkanolamine salts or on fatty amines, preferably in the form of their organic or inorganic salts.

Whereas both classes of substances can be used without difficulty in dip lubrication, they are attended by a number of disadvantages in the central chain lubrication systems typically in use today. Thus, DE-A-23 13 330 describes soap-based lubricants containing aqueous mixtures of $C_{16-18}$ fatty acid salts and surface-active substances. Soap-based lubricants such as these have the following disadvantages:

1. They react with the hardness ions in water, i.e. the alkaline earth metal ions, and other ingredients of water to form poorly soluble metal soaps, so-called primary alkaline earth metal soaps.
2. A reaction takes place between the soap-based lubricants and carbon dioxide dissolved in water or in the product to be bottled.
3. The in-use solution thus prepared is always germ-promoting.
4. Where hard water is used, ion exchangers have to be employed to soften the water which means an additional source of germs (and is therefore hardly encountered in practice) or, alternatively, products of high complexing agent content have to be used which is ecologically unsafe.
5. Increased foaming occurs which can cause problems in particular at the bottle inspector (automatic bottle control) and results in greater wetting of the transport containers.
6. Most of these products contain solvents.
7. The cleaning effect of the products is poor so that separate cleaning is necessary.
8. Corresponding soap-based lubricant preparations show pH-dependent performance.
9. In addition, soap-based lubricant preparations are dependent on the water temperature.
10. Soap-based lubricants show poor stability in storage, particularly at low temperatures.
11. The EDTA (ethylenediamine tetraacetate) present in many products is known to have poor biodegradability.
12. Soap-based lubricant preparations are not suitable for all plastic transport containers because, in many cases, they give rise to stress cracking in the transport container.

Besides soap-based lubricants, lubricants based on fatty amines are mainly used. Thus, DE-A-36 31 953 describes a process for lubricating chain-type bottle conveyors in bottling factories, more particularly in breweries, and for cleaning the conveyors with a liquid cleaning composition, characterized in that the chain-type bottle conveyors are lubricated with belt lubricants based on neutralized primary fatty amines which preferably contain 12 to 18 carbon atoms and which have an unsaturated component of more than 10%.

EPA-0 372 628 discloses fatty amine derivatives corresponding to the following formulae:

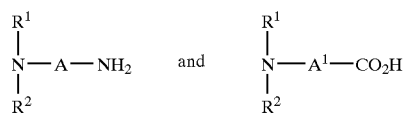

in which $R^1$ is a saturated or unsaturated, branched or linear alkyl group containing 8 to 22 carbon atoms, $R^2$ is hydrogen, an alkyl or hydroxyalkyl group containing 1 to 4 carbon atoms or —A—NH$_2$, A is a linear or branched alkylene group containing 1 to 8 carbon atoms and $A^1$ is a linear or branched alkylene group containing 2 to 4 carbon atoms, as lubricants.

In addition, lubricants based on N-alkylated fatty amine derivatives which contain at least one secondary and/or tertiary amine are known from DE-A-39 05 548.

DE-A-42 06 506 relates to soapless lubricants based on amphoteric compounds, primary, secondary and/or tertiary amines and/or salts of such amines corresponding to general formulae (I), (IIa), (IIb), (IIIa), (IIIb), (IIIc), (IVa) and (IVb):

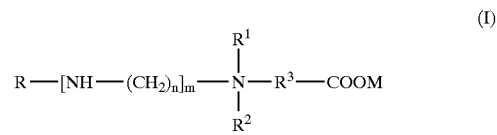

and/or

in which

R is a saturated or mono- or polyunsaturated, linear or branched alkyl group containing 6 to 22 carbon atoms which may optionally be substituted by —OH, —NH$_2$, —NH—, —CO—, —(CH$_2$CH$_2$O)$_l$— or —(CH$_2$CH$_2$CH$_2$O)$_l$—, R$^1$ is hydrogen, an alkyl group containing 1 to 4 carbon atoms, a hydroxyalkyl group containing 1 to 4 carbon atoms or a group —R$^3$COOM, R$^2$ is hydrogen, an alkyl group containing 1 to 4 carbon atoms or a hydroxyalkyl group containing 1 to 4 carbon atoms, but only where M represents a negative charge, R$^3$ is a saturated or mono- or polyunsaturated, linear or branched alkyl group containing 1 to 12 carbon atoms which may optionally be substituted by —OH, —NH$_2$, —NH—, —CO—, —(CH$_2$CH$_2$O)$_l$— or —(CH$_2$CH$_2$CH$_2$O)$_l$—, R$^4$ is a substituted or unsubstituted, linear or branched, saturated or mono- or polyunsaturated alkyl group containing 6 to 22 carbon atoms which may contain at least one amine, imine, hydroxy, halogen and/or carboxy group as substituent, a substituted or unsubstituted phenyl group which may contain at least one amine, imine, hydroxy, halogen, carboxy and/or a linear or branched, saturated or mono- or polyunsaturated alkyl group containing 6 to 22 carbon atoms as substituent, R$^5$ is hydrogen or—independently of R$^4$—has the same meaning as R$^4$, X$^{31}$ is an anion from the group consisting of amidosulfonate, nitrate, halide, sulfate, hydrogen carbonate, carbonate, phosphate or R$^6$—COO$^-$ where R$^6$ is hydrogen, a substituted or unsubstituted, linear or branched alkyl group containing 1 to 20 carbon atoms or alkenyl group containing 2 to 20 carbon atoms, which may contain at least one hydroxy, amine or imine group as substituent, or a substituted or unsubstituted phenyl group which may contain an alkyl group with 1 to 20 carbon atoms as substituent, and R$^7$ and R$^8$ independently of one another represent a substituted or unsubstituted, linear or branched alkyl group containing 1 to 20 carbon atoms or alkenyl group containing 2 to 20 carbon atoms which may contain at least one hydroxy, amine or imine group as substituent, or a substituted or unsubstituted phenyl group which may contain an alkyl group with 1 to 20 carbon atoms as substituent, M is hydrogen, alkali metal, ammonium, an alkyl group containing 1 to 4 carbon atoms, a benzyl group or a negative charge, n is an integer of 1 to 12, m is an integer of 0 to 5 and l is a number of 0 to 5, containing alkyl dimethylamine oxides and/or alkyl oligoglycosides as nonionic surfactants.

EP-B-629 234 discloses a lubricant combination consisting of a) one or more compounds corresponding to the following formula:

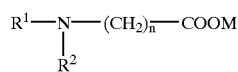

in which

R$^1$ is a saturated or mono- or polyunsaturated, linear or branched alkyl group containing 6 to 22 carbon atoms which may optionally be substituted by —OH, —NH$_2$—, —NH—, —CO—, halogen or a carboxyl group, R$^2$ is a carboxyl group containing 2 to 7 carbon atoms, M is hydrogen, alkali metal, ammonium, an alkyl group containing 1 to 4 carbon atoms or a benzyl group and n is an integer of 1 to 6, b) at least one organic carboxylic acid selected from monobasic or polybasic, saturated or mono- or polyunsaturated carboxylic acids containing 2 to 22 carbon atoms, c) optionally water and additives and/or auxiliaries.

WO 94/03562 describes a lubricant concentrate based on fatty amines and optionally typical diluents or auxiliaries and additives, characterized in that it contains at least one polyamine derivative of a fatty amine and/or a salt of such an amine, the percentage content of the polyamine derivatives of fatty amines in the formulation as a whole being from 1 to 100% by weight.

In one preferred embodiment of WO 94/03562, this lubricant concentrate contains at least one polyamine derivative of a fatty amine corresponding to the following general formula:

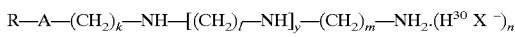

in which

R is a substituted or unsubstituted, linear or branched, saturated or mono- or polyunsaturated alkyl group containing 6 to 22 carbon atoms, the substituents being selected from amino, imino, hydroxy, halogen and carboxy, or a substituted or unsubstituted phenyl group, the substituents being selected from amino, imino, hydroxy, halogen, carboxy and a linear or branched, saturated or mono- or polyunsaturated alkyl group containing 6 to 22 carbon atoms, A represents either —NH— or —O—, X$^-$ is an anion of an inorganic or organic acid, k, l and m independently of one another are integers of 1 to 6, y is 0, 1, 2 or 3 where A=—NH— or 1, 2, 3 or 4 where A=—O— and n is an integer of 0 to 6.

The problem addressed by the present invention was to enable conveyor belt installations to be lubricated with silicone-containing formulations, to further reduce water consumption and to achieve high material compatibility with plastic containers.

The present invention relates to the use of formulations containing at least 1% by weight and preferably at least 5% by weight, based on the formulation as a whole, of at least one polysiloxane preferably selected from the groups of linear, branched, cyclic and crosslinked polysiloxanes for lubricating conveyor belt installations in the food industry, the formulations being applied to the conveyor belt installations directly, i.e. without dilution with water in the food factory, via an application system which is preferably in direct contact with the surfaces to be lubricated during application or which, in another preferred embodiment, is in the form of a spray applicator. In one preferred use according to the invention, the formulations additionally contain at least one component selected from fluorine and polyhydroxy compounds and/or ethers and esters thereof.

Where fluorine compounds are used in the formulations to be used in accordance with the invention, they are preferably selected from the groups of a) perfluorinated or partly fluorinated monomeric organic compounds, b) pure and mixed dimers and oligomers based on at least one perfluorinated or partly fluorinated organic monomer, c) pure and mixed polymers based on at least one perfluorinated or partly fluorinated organic monomer.

According to the invention, the definition of the boundary between oligomers and polymers is based on the generally known characterization of polymers which are made up of so many identical or similar low molecular weight units (monomers) that the physical properties of these substances, particularly their viscoelasticity, do not change significantly when the number of units is increased or reduced by one unit. This is generally the case when the average molecular weight of the "polymers" is 10,000 g/mole or more.

The term oligomers is used for the low molecular weight dimers, trimers and other lower members of the polymer-homolog series.

In one preferred embodiment, the fluorine compounds a) comprise at least perfluorinated and partly fluorinated surfactants, alkanes, ethers and amines, the formulations used in accordance with the invention in one particularly preferred embodiment containing ammonium perfluoroalkyl sulfonates, lithium perfluoroalkyl sulfonates, potassium perfluoroalkyl sulfonates, amine perfluoroalkyl sulfonates, sodium perfluoroalkyl sulfonates, potassium fluoroalkyl carboxylates, quaternary fluorinated alkyl ammonium iodides, ammonium perfluoroalkyl carboxylates, fluorinated alkyl polyoxyethylene ethanols, fluorinated alkyl alkoxylates, fluorinated alkyl esters in concentrations of 0.001 to 10%. The fluorinated components of group c) are preferably perfluorinated and/or partly fluorinated alkoxy polymers which, in one particularly preferred embodiment, are obtainable from the copolymerization of tetrafluoroethylene and perfluoroalkoxyvinyl ethers.

In another preferred embodiment, the formulations to be used in accordance with the invention contain at least perfluorinated and/or partly fluorinated polyethers from group c).

Where polyhydroxy compounds are used in the formulations to be used in accordance with the invention, they are preferably selected from the groups of polyalcohols and carbohydrates and, in one particularly preferred embodiment, from polyhydric alcohols, preferably alkanediols, alkanetriols and most preferably glycerol and the polyethers derived therefrom and also glucose, arabinose, ribulose, fructose and the oligo- and/or polysaccharides derived therefrom and esters and ethers thereof.

In another preferred embodiment, the formulations to be used in accordance with the invention are present in the form of one-component liquids, solutions, gels, emulsions, pastes, dispersions.

In one preferred embodiment, the formulations to be used in accordance with the invention additionally contain at least one antimicrobial component selected from the groups of alcohols, aldehydes, antimicrobial acids, carboxylic acid esters, acid amides, phenols, phenol derivatives, diphenyls, diphenyl alkanes, urea derivatives, oxygen and nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propynyl butyl carbamate, iodine, iodophors, peroxides, the formulations to be used in accordance with the invention in one particularly preferred embodiment containing one or more compounds selected from ethanol, n-propanol, i-propanol, butane-1,3-diol, phenoxyethanol, 1,2-propylene glycol, glycerol, undecylenic acid, citric acid, 2-benzyl-4-chlorophenol, 2,2'-methylene-bis-(6-bromo-4-chlorophenol), 2,4,4'-trichloro-2'-hydroxydiphenyl ether, N-(4-chlorophenyl)-N-(3,4-dichlorophenyl)-urea, N,N'-(1, 10-decanediyldi-1-pyridinyl-4-ylidene)-bis-(1-octaneamine)-dihydrochloride, N,N'-bis-(4-chlorophenyl)-3,12-diimino-2,4,11,13-tetraazatetradecane diimidoamide, quaternary ammonium compounds or alkyl amines, guanidines, amphoteric surfactants as antimicrobial components.

In another preferred embodiment, the formulations to be used in accordance with the invention contain other components selected from the groups of surfactants and solubilizing agents, at least one alkyl polyglycoside being present as surfactant in a particularly preferred embodiment. Other preferred constituents are fatty alkylamines and/or alkoxylates thereof, more particularly cocofatty amine ethoxylates, and/or imidazoline compounds and/or amphoteric surfactants and/or nonionic surfactants and/or ether carboxylic acids and/or ether amine compounds. In another preferred embodiment, paraffin compounds are added to the formulations to be used in accordance with the invention.

In practice, the formulations to be used in accordance with the invention are applied to the chain conveyors. In the most favorable case, the transport of the containers on the conveyors is not accompanied by foaming. By comparison with conventional lubricants which are diluted with water by a factor of more than 100 in automatic conveyor installations, the formulations to be used in accordance with the invention reduce frictional resistance between the conveyor and the containers transported thereon by more than 20% by for the same quantities by weight of active lubricating components applied to the conveyor installation over a certain period of time. This is demonstrated by the following Examples.

EXAMPLE 1

A comparison formulation 1 which contains 5% by weight of coconut propylenediamine and which is adjusted to pH 7 with acetic acid is applied to the chain conveyors in a concentration in water of 0.2% through a nozzle block comprising five nozzles each capable of spraying 5 liters per hour. 50 ml of the comparison formulation or ca. 2.5 g of the coconut propylenediamine are thus applied to the conveyor chains over a period of 1 hour. This test is carried out for 10 hours. According to the invention, the coefficient of friction between the bottles and the stainless steel conveyor chains is defined as the ratio of the tractive weight applied, for example, to a spring balance when an attempt is made to hold a bottle still while the conveyor is moving to the weight of that bottle.

Where the Comparison Example described above is used, the coefficient of friction $\mu$ is 0.10. When spraying is stopped, the friction coefficient increases rapidly and the bottles fall over after only a few minutes.

In the Comparison Example, a total of 25 ml of lubricating coconut propylenediamine raw materials is applied to the conveyor chains over the total test duration of 10 hours. In a second test, 25 ml of a formulation to be used in accordance with the invention consisting of a 35% aqueous polydimethyl siloxane dispersion is distributed over the chain conveyors with a cloth. The coefficient of friction between the bottles and the chain conveyor is then measured over a period of 10 hours under exactly the same conditions as in Comparison Example 1. The coefficient of friction $\mu$ is about 0.05 over the entire test duration of 10 hours. This Example shows that the friction coefficient between the bottles and the conveyor system can be reduced by more than 20% and, in the present case, even by more than 40%.

Another preferred embodiment of the present invention is the use of the formulations to be used in accordance with the invention for the conveying of plastic containers, the plastic containers in one particularly preferred embodiment containing at least one polymer selected from the groups of polyethylene terephthalates (PET), polyethylene naphthenates (PEN), polycarbonates (PC), PVC. In one most particularly preferred embodiment, the containers are PET bottles.

EXAMPLE 2

In a laboratory test, the stress cracking of a Comparison Example based on 5% by weight coconut propylene diamine and 5% by weight dimethyl lauryl amine adjusted to pH 7 with acetic acid is measured by comparison with the stress cracking of a 25% aqueous polydimethyl siloxane dispersion.

According to the test specification, PET bottles are filled with water and conditioned with carbon dioxide in such a way that a pressure of about 7 bar is present inside the bottles. The base cups of the bottles are then dipped in the formulation of the Comparison Example and the Example to be used in accordance with the invention and are placed in a Petri dish for 24 hours. Thereafter the bottles are opened, emptied and their base cups are rinsed with water. Visual inspection of the base cups of the bottles shows that, in the test with the Comparison Example, many stress cracks of average depth (classification C) are present whereas the test with the Example to be used in accordance with the invention produces only a few stress cracks of minimal depth (classification A). The stress cracks are classified in accordance with the reference images appearing in Chapter IV-22 of the book entitled "CODE OF PRACTICE—Guidelines for an Industrial Code of Practice for Refillable PET Bottles", Edition 1, 1993–1994.

Example 2 shows that the formulations to be used in accordance with the invention have advantages over typical commercial amine-based products used as lubricants in the conveying of plastic bottles.

In another preferred embodiment, the formulations to be used in accordance with the invention are used for conveying paperboard packs.

In another preferred use, the conveying surfaces of the conveyor belts are made of plastic—in one particularly preferred embodiment of polyacetal and polyethylene.

In another preferred embodiment, the conveying surfaces of the conveyor belt are made of metal—in one particularly preferred embodiment stainless steel.

In another preferred embodiment, additional antimicrobial agents, more particularly organic peracids, chlorine dioxide or ozone, are additionally incorporated in the formulations to be used in accordance with the invention through separate feed systems either before or after application of the formulations.

In another preferred embodiment, the formulations to be used in accordance with the invention are applied to the conveyor belts without dilution with water using an aid selected from paint brushes, sponges, rollers, cloths, brushes, wipers, rubber, spray nozzles. In another preferred embodiment, the formulations to be used in accordance with the invention are diluted with water in automatic conveyor systems and the resulting solution is applied to the conveyors through metering systems, the dilution factor being between 10,000 and 100. In another preferred embodiment, the formulations to be used in accordance with the invention are selected and applied in such a way that there is no further proliferation of microorganisms on surfaces in contact with the formulations or solution. In one most particularly preferred embodiment, the number of microorganisms is reduced.

The present invention also relates to chain lubricants which, based on the formulation as a whole, contain at least 1% by weight and preferably at least 5% by weight of at least one polysiloxane and, in addition, at least one polyhydroxy compound and/or an organic fluorine compound, the sum total of polysiloxane and polyhydroxy compound and/or organic fluorine compound making up at least 15% by weight of the formulation as a whole in one preferred embodiment.

Where fluorine compounds are used in the formulations to be used in accordance with the invention, they are preferably selected from the groups of a) perfluorinated or partly fluorinated monomeric organic compounds, b) pure and mixed dimers and oligomers based on at least one perfluorinated or partly fluorinated organic monomer, c) pure and mixed polymers based on at least one perfluorinated or partly fluorinated organic monomer.

According to the invention, the definition of the boundary between oligomers and polymers is based on the generally known characterization of polymers which are made up of so many identical or similar low molecular weight units (monomers) that the physical properties of these substances, particularly their viscoelasticity, do not change significantly when the number of units is increased or reduced by one unit. This is generally the case when the average molecular weight of the "polymers" is 10,000 g/mole or more.

The term oligomers is used for the low molecular weight dimers, trimers and other lower members of the polymer-homolog series.

In one preferred embodiment, the fluorine compounds a) comprise at least perfluorinated and partly fluorinated surfactants, alkanes, ethers and amines, the formulations used in accordance with the invention in one particularly preferred embodiment containing ammonium perfluoroalkyl sulfonates, lithium perfluoroalkyl sulfonates, potassium perfluoroalkyl sulfonates, amine perfluoroalkyl sulfonates, sodium perfluoroalkyl sulfonates, potassium fluoroalkyl carboxylates, quaternary fluorinated alkyl ammonium iodides, ammonium perfluoroalkyl carboxylates, fluorinated alkyl polyoxyethylene ethanols, fluorinated alkyl alkoxylates, fluorinated alkyl esters In concentrations of 0.001 to 10%. The fluorinated components of group c) are preferably perfluorinated and/or partly fluorinated alkoxy polymers which, in one particularly preferred embodiment, are obtainable from the copolymerization of tetrafluoroethylene and perfluoroalkoxyvinyl ethers.

In another preferred embodiment, the formulations to be used in accordance with the invention contain at least perfluorinated and/or partly fluorinated polyethers from group c).

Where polyhydroxy compounds are used in the formulations to be used in accordance with the invention, they are preferably selected from the groups of polyalcohols and carbohydrates and, in one particularly preferred embodiment, from polyhydric alcohols, preferably alkanediols, alkanetriols and most preferably glycerol and the polyethers derived therefrom and also glucose, arabinose, ribulose, fructose and the oligo- and/or polysaccharides derived therefrom and esters and ethers thereof.

The advantage of the use according to the invention and of the chain lubricants according to the invention is that water consumption is significantly reduced. Since the belt lubricating solution is not collected and re-used in the prior art, the process in use today involves an enormous waste of resources. Another advantage is that, providing it is properly applied, hardly any of the formulation drips onto the floor. This results in greater safety and in purely visual advantages in the factory. In addition, soil occurring has sometimes been seen to be repelled by the conveyor belts conditioned with the formulation.

What is claimed is:

1. A method of lubricating the interface between a container and a moving conveyor surface to reduce frictional resistance between the conveyor and the containers transported thereon, the method comprising applying, by direct contact with no dilution of a lubricant concentrate, an effective amount of a liquid lubricant composition between a container and a contact surface of the moving conveyor to reduce frictional resistance between the conveyor and the containers transported thereon, the lubricant comprising an aqueous solution comprising at least one weight percent of a polysiloxane composition based on the liquid lubricant.

2. The method of claim the 1 wherein the liquid lubricant is sprayed directly onto at least a portion of the contact surface of the moving conveyor.

3. The method of claim the 1 wherein a liquid lubricant is applied to the moving conveyor through a mechanical device in direct contact with the conveyor surface.

4. The method of claim 1 wherein the liquid lubricant additionally comprises a fluorinated organic compound.

5. The method of claim 1 wherein the fluorinated monomeric organic compound comprises a perfluorinated monomeric organic compound.

6. The method of claim 4 wherein the fluorinated organic compound comprises a compound selected from the group consisting of a dimer, an oligomer and mixtures thereof of at least one fluorinated organic monomer.

7. The method of claim 4 wherein the fluorinated organic compound comprises a compound comprising a polymer comprising at least one fluorinated organic monomer containing less than 70 wt % fluorine, based on the total weight of monomer in the polymer.

8. The method of claim 5 wherein the fluorinated monomeric organic compound comprises a fluorinated surfactant, a fluorinated alkane, a fluorinated ether, a fluorinated amine or mixtures thereof.

9. The method of claim 1 wherein the lubricant is present in the form of a gel, emulsion, paste or dispersion of a liquid lubricant in an aqueous phase.

10. The method of claim 1 wherein the formulations additionally contain at least one antimicrobial component selected from the group of alcohol, an aldehyde, an antimicrobial acid, a carboxylic acid ester, an acid amide, a phenol, a phenol derivative, a diphenyl, a diphenyl alkane, a urea derivative, an oxygen and nitrogen acetal and formal, a benzamidine, a isothiazoline, a phthalimide derivative, a pyridine derivative, an antimicrobial surface-active compound, a guanidine, an antimicrobial amphoteric compound, a quinoline, a 1,2-dibromo-2,4-dicyanobutane, a iodo-2-propynyl butyl carbamate, iodine, an iodophor, a peroxide or mixtures thereof.

11. The method claimed in claim 1, wherein the formulations contain one or more antimicrobial compounds selected from ethanol, n-propanol, i-propanol, butane-1,3-diol, phenoxyethanol, 1,2-propylene glycol, glycerol, undecylenic acid, citric acid, 2-benzyl-4-chlorophenol, 3,3'-methylene-bis(6-bromo-4-chlorophenol), 2,4,4'-trichlor-2'-hydroxydiphenyl ether, N-(4-chlorophenyl)-N-(3,4-dichlorophenyl)-urea, N,N'-(1,10-decanediyldi-1-pyridinyl-4-ylidene)-bis-(1-octaneamine)-dihydrochloride, N,N'-bis-(4-chlorophenyl)3,12-diimino-2,4,11,13-tetraazatetradecane diimidoamide, quaternary ammonium compounds or alkyl amines, guanidines, amphoteric surfactants and mixtures thereof.

12. The method of claim 1 wherein the formulations additionally contain at least one component selected from the group of polyhydroxy compounds.

13. The method of claim 12 wherein the polyhydroxy compounds are selected from the groups of polyalcohols and carbohydrates.

14. The method of claim 12 wherein at the polyhydroxy compound comprises an alkanediol, an alkanetriols, a polyethers derived thereof, glucose, arabinose, ribulose, fructose, the oligo- or polysaccharide derived thereof and their esters and ethers.

15. The method of claim 1 wherein the formulations additionally contain at least one fluorinated component selected from the group of fluorinated polyhydroxy compounds.

16. The method of claim 15 wherein the polyhydroxy compounds are selected from the groups of polyalcohols and carbohydrates.

17. The method of claim 15 where at least one polyhydroxy component selected from a polyhydroxy alcohol, an alkanediol, an alkanetriols, polyethers derived thereof, glucose, arabinose, ribulose, fructose, the oligo- or polysaccharides derived thereof and their esters and ethers.

18. The method of claim 1 wherein the formulations contain other components selected from the groups of surfactants and solubilizing agents.

19. The method of claim 18 wherein the lubricant comprises at least one alkyl polyglycoside.

20. The method of claim 1 wherein the formulations have a water content of less than 20% by weight, based on the formulation as a whole.

21. The method of claim 1 wherein the water content is less than 10% by weight, based on the formulation as a whole.

22. The method of claim 1 wherein substantially no foam is formed from the lubricant during the conveying of the containers on the conveyors.

23. The method of claim 1 wherein, by comparison with conventional lubricants which are diluted with water by a factor of more than 100 in automatic conveyor installations, the frictional resistance between the conveyor and the containers transported thereon are reduced by more than 20% for the same quantities by weight of active lubricating components applied to the conveyor.

24. The method of claim 1 for the conveying of a plastic container.

25. The method of claim 24 wherein the plastic container comprises at least one polymer selected from the groups of polyethylene terephthalate (PET), polyethylene naphthenate (PEN), polycarbonate (PC), polyvinyl chloride (PVC).

26. The method of claim 24 wherein the plastic containers are 2 liter bottles.

27. The method of claim 1 for the conveying of containers in paperboard packs.

28. The method of claim 1 wherein the conveying surfaces of the conveyor system are made of plastic.

29. The method of claim 1 wherein the contact surfaces of the conveyor system are made of metal.

30. The method of claim 1 wherein the metal comprises aluminum and the container comprises a can.

31. The method of claim 1 wherein additional antimicrobial agents are separately added during application.

32. The method of claim 31 wherein the antimicrobial agent comprises an organic peracid, chlorine dioxide or ozone.

33. The method of claim 1 wherein the formulation is applied to the conveyor belts without preliminary dilution with water using an applicator selected from a brush, a sponge, a roller, a wiper or a spray.

34. The method of claim 1 wherein there is no further proliferation of microorganisms on surfaces in contact with the lubricant.

35. The method of claim 1 wherein the number of microorganisms on surfaces in contact with the lubricant is reduced.

36. The method of claim 1 for the conveying of a food container.

37. An aqueous lubricant formulated to lubricate the interface between a moving conveyor and a container to reduce frictional resistance between the conveyor and the containers transported thereon, the lubricant composition comprising an aqueous solution comprising at least one weight percent of a polysiloxane polymer based on the liquid lubricant.

38. The lubricant of claim 37 wherein the liquid lubricant additionally comprises a fluorinated organic compound.

39. The lubricant of claim 37 wherein the fluorinated monomeric organic compound comprises a perfluorinated monomeric organic compound.

40. The lubricant of claim 38 wherein the fluorinated organic compound comprises a compound selected from the group consisting of a dimer, an oligomer and mixtures thereof of at least one fluorinated monomer.

41. The lubricant of claim 38 wherein the fluorinated organic compound comprises a compound comprising a polymer comprising at least one fluorinated organic monomer containing less than 70 wt % fluorine, based on the total weight of monomer in the polymer.

42. The lubricant of claim 39 wherein the fluorinated monomeric organic compound comprises a fluorinated surfactant, a fluorinated alkane, a fluorinated ether, a fluorinated amine or mixtures thereof.

43. The lubricant of claim 40 wherein the organic monomer is a perfluorinated organic monomer.

44. The lubricant of claim 43 wherein tab lubricant comprises mixed oligomers of a fluorinated organic monomer.

45. The lubricant of claim 42 wherein compounds obtainable by reacting tetrafluoroethylene and a perfluoroalkoxy vinyl ethers.

46. The lubricant of claim 42 wherein the formulation comprises a form of liquid solution or emulsion.

47. The lubricant of claim 37 wherein the formulation comprises at least one antimicrobial component selected from the group of alcohol, an aldehyde, an antimicrobial acid, a carboxylic acid ester, an acid amide, a phenol, a phenol derivative, a diphenyl, a diphenyl alkane, a urea derivative, an oxygen and nitrogen acetal and formal, a benzamidine, a isothiazoline, a phthalimide derivative, a pyridine derivative, an antimicrobial surface-active compound, a guanidine, an antimicrobial amphoteric compound, a quinoline, a 1,2-dibromo-2,4-dicyanobutane, a iodo-2-propynyl butyl carbamate, iodine, an iodophor, a peroxide or mixtures thereof.

48. The lubricant in claim 37 wherein the formulations contain an antimicrobial compound selected from ethanol, n-propanol, i-propanol, butane-1,3-diol, phenoxyethanol, 1,2-propylene glycol, glycerol, undecylenic acid, citric acid, 2-benzyl-4-chlorophenol, 3,3'-methylene-bis(6-bromo-4chlorophenol), 2,4,4'-trichlor-2'-hydroxydiphenyl ether, N-(4-chlorophenyl)-N-(3,4-dichlorophenyl)-urea, N,N'(1, 10-decanediyldi-1-pyridinyl-4-ylidene)-bis-(1-octaneamine)-dihydrochloride, N,N'-bis(4-chlorphenyl)3, 12-diimino-2,4,11,13-tetraazatetradecane diimidoamide, a quaternary ammonium compound or an alkyl Amine, a guanidine, or an amphoteric surfactant.

49. The lubricant of claim 37 wherein the formulations additionally contain at least one fluorinated polyhydroxy compound.

50. The lubricant of claim 49 wherein the polyhydroxy compounds are selected from the groups of polyalcohols and carbohydrates.

51. The lubricant of claim 49 wherein at least one polyhydroxy component selected from polyhydric alcohol, an alkanediol, an alkanetriols and the polyethers derived thereof and glucose, arabinose, ribulose, fructose and the oligo- and/or polysaccharides derived thereof and their esters and ethers.

52. The lubricant of claim 49 wherein the polyhydroxy compound comprises an alkanediol or an alkanetriols.

53. The lubricant of claim 37 wherein the formulation comprises a surfactant or a solubilizing agent.

54. The lubricant of claim 53 comprising an alkyl polyglycoside.

55. The lubricant of claim 37 wherein the formulations have a water content of less than 20% by weight, based on the formulation as a whole.

56. The lubricant of claim, 37 wherein the water content is below 10% by weight, based on the formulation as a whole.

57. The lubricant of claim 37 wherein, by comparison with conventional lubricants which are diluted with water by a factor of more than 100 in automatic conveyor installations, the frictional resistance between the conveyor and the containers transported thereon is reduced by more than 20% for the same quantities by weight of active lubricating components applied to the conveyor installation over a certain period of time.

58. The lubricant of claim 37 wherein additional antimicrobial agents are separately added during application.

59. The lubricant of claim 58 wherein the antimicrobial agent comprises an organic peracid, chlorine dioxide or ozone.

60. The lubricant of claim 37 wherein about one part by volume of lubricant is diluted with about 100 and 10,000 parts by volume of diluent.

* * * * *